US007837673B2

(12) United States Patent
Vogel

(10) Patent No.: US 7,837,673 B2
(45) Date of Patent: Nov. 23, 2010

(54) WOUND IRRIGATION DEVICE

(75) Inventor: Richard C. Vogel, Potomac, MD (US)

(73) Assignee: Innovative Therapies, Inc., Gaithersburg, MD (US)

(*) Notice: Subject to any disclaimer, the term of this patent is extended or adjusted under 35 U.S.C. 154(b) by 0 days.

(21) Appl. No.: 11/237,880

(22) Filed: Sep. 29, 2005

(65) Prior Publication Data

US 2007/0032762 A1     Feb. 8, 2007

Related U.S. Application Data

(63) Continuation of application No. 11/198,148, filed on Aug. 8, 2005, now abandoned.

(51) Int. Cl.
*A61M 27/00* (2006.01)
(52) U.S. Cl. .................. 604/543; 604/323; 604/325
(58) Field of Classification Search .................. 604/313, 604/540–541, 543, 317, 323–325, 327
See application file for complete search history.

(56) References Cited

U.S. PATENT DOCUMENTS

| 2,232,254 A | 2/1941 | Morgan |
| 2,338,339 A | 1/1944 | LeMere et al. |
| 2,547,758 A | 4/1951 | Keeling |
| 2,969,057 A | 1/1961 | Simmons |
| 3,026,526 A | 3/1962 | Montrose |
| 3,026,874 A | 3/1962 | Stevens |
| 3,367,332 A | 2/1968 | Groves |
| 3,478,736 A | 11/1969 | Roberts et al. |
| 3,481,326 A | 12/1969 | Schamblin |
| 3,486,504 A | 12/1969 | Austin, Jr. |
| 3,610,238 A | 10/1971 | Rich, Jr. |
| 3,682,180 A | 8/1972 | McFarlane |
| 3,826,254 A | 7/1974 | Mellor |
| 3,874,387 A | 4/1975 | Barbieri |
| 3,896,810 A | 7/1975 | Akiyama |
| 3,908,664 A | 9/1975 | Loseff |
| 3,954,105 A | 5/1976 | Nordby et al. |
| 3,993,080 A | 11/1976 | Loseff |
| RE29,319 E | 7/1977 | Nordby et al. |

(Continued)

FOREIGN PATENT DOCUMENTS

DE      28 09-828 A1     9/1978

(Continued)

OTHER PUBLICATIONS

Chinn, Steven D et al., "*Closed Wound Suction Drainage*", The Journal of Foot Surgery, vol. 24, No. 1, 1985, pp. 76-81.

(Continued)

*Primary Examiner*—Michele Kidwell
(74) *Attorney, Agent, or Firm*—Cooley LLP

(57) ABSTRACT

An apparatus includes a fluid permeable dressing and a cover membrane configured to extend over the fluid permeable dressing. A tube is coupled to the fluid permeable dressing and is configured to apply suction through the fluid permeable dressing. A fluid reservoir is coupled to the cover membrane, the fluid vessel including an inlet port configured to receive a fluid and an outlet port fluidically coupled to the fluid permeable dressing.

28 Claims, 9 Drawing Sheets

U.S. PATENT DOCUMENTS

| | | | |
|---|---|---|---|
| 4,080,970 A | 3/1978 | Miller | |
| 4,112,947 A | 9/1978 | Nehring | |
| 4,149,541 A | 4/1979 | Gammons et al. | |
| 4,169,563 A | 10/1979 | Leu | |
| 4,172,455 A | 10/1979 | Beaussant | |
| 4,224,945 A | 9/1980 | Cohen | |
| 4,250,882 A | 2/1981 | Adair | |
| 4,256,109 A | 3/1981 | Nichols | |
| 4,261,363 A | 4/1981 | Russo | |
| 4,275,721 A | 6/1981 | Olson | |
| 4,297,995 A | 11/1981 | Golub | |
| 4,373,519 A | 2/1983 | Errede et al. | |
| 4,382,441 A | 5/1983 | Svedman | |
| 4,392,853 A | 7/1983 | Muto | |
| 4,419,097 A | 12/1983 | Rowland | |
| 4,441,357 A | 4/1984 | Khan et al. | |
| 4,469,092 A | 9/1984 | Marshall et al. | |
| 4,475,909 A | 10/1984 | Eisenberg | |
| 4,480,638 A | 11/1984 | Schmid | |
| 4,525,166 A | 6/1985 | Leclerc | |
| 4,527,064 A | 7/1985 | Anderson | |
| 4,540,412 A | 9/1985 | Van Overloop | |
| 4,543,100 A | 9/1985 | Brodsky | |
| 4,569,674 A | 2/1986 | Phillips et al. | |
| 4,573,965 A | 3/1986 | Russo | |
| 4,605,399 A | 8/1986 | Weston et al. | |
| 4,608,041 A | 8/1986 | Neilsen | |
| 4,624,656 A | 11/1986 | Clark et al. | |
| 4,640,688 A | 2/1987 | Hauser | |
| 4,661,093 A | 4/1987 | Beck et al. | |
| 4,710,165 A | 12/1987 | McNeil et al. | |
| 4,713,052 A | 12/1987 | Beck | |
| 4,743,232 A | 5/1988 | Kruger | |
| 4,755,168 A | 7/1988 | Romanelli et al. | |
| 4,759,354 A | 7/1988 | Quarfoot | |
| 4,764,167 A | 8/1988 | Tu | |
| 4,765,316 A | 8/1988 | Marshall | |
| 4,778,456 A | 10/1988 | Lokken | |
| 4,820,265 A | 4/1989 | DeSatnick et al. | |
| 4,820,284 A | 4/1989 | Hauri | |
| 4,834,110 A | 5/1989 | Richard | |
| 4,836,192 A | 6/1989 | Abbate | |
| 4,838,883 A | 6/1989 | Matsuura | |
| 4,840,187 A | 6/1989 | Brazier | |
| 4,851,545 A | 7/1989 | Song et al. | |
| 4,863,449 A | 9/1989 | Therriault et al. | |
| 4,878,901 A | 11/1989 | Sachse | |
| 4,906,233 A | 3/1990 | Moriuchi et al. | |
| 4,909,244 A | 3/1990 | Quarfoot et al. | |
| 4,917,112 A | 4/1990 | Kalt | |
| 4,921,492 A | 5/1990 | Schultz et al. | |
| 4,925,447 A | 5/1990 | Rosenblatt | |
| 4,931,519 A | 6/1990 | Song et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,969,881 A | 11/1990 | Viesturs | |
| 5,035,884 A | 7/1991 | Song et al. | |
| 5,086,764 A | 2/1992 | Gilman | |
| 5,100,396 A | 3/1992 | Zamierowski | |
| 5,106,362 A | 4/1992 | Gilman | |
| 5,113,871 A | 5/1992 | Viljanto et al. | |
| 5,149,331 A | 9/1992 | Ferdman et al. | |
| 5,176,663 A | 1/1993 | Svedman | |
| 5,228,431 A | 7/1993 | Giarretto | |
| 5,261,893 A | 11/1993 | Zamierowski | |
| 5,312,690 A | 5/1994 | Fukuda et al. | |
| 5,358,494 A * | 10/1994 | Svedman | 604/313 |
| 5,527,293 A | 6/1996 | Zamierowski | |
| 5,636,643 A | 6/1997 | Argenta et al. | |
| 5,645,081 A | 7/1997 | Argenta et al. | |
| 5,733,545 A | 3/1998 | Hood, III | |
| 5,779,657 A | 7/1998 | Daneshvar | |
| 6,040,493 A | 3/2000 | Cooke et al. | |
| 6,071,267 A | 6/2000 | Zamierowski | |
| 6,087,549 A | 7/2000 | Flick | |
| 6,142,982 A * | 11/2000 | Hunt et al. | 604/313 |
| 6,196,992 B1 | 3/2001 | Keilman et al. | |
| 6,398,767 B1 | 6/2002 | Fleischmann | |
| 6,432,438 B1 | 8/2002 | Shukla | |
| 6,458,109 B1 | 10/2002 | Henley et al. | |
| 6,551,280 B1 | 4/2003 | Knighton et al. | |
| 6,695,823 B1 | 2/2004 | Lina et al. | |
| 6,695,824 B2 | 2/2004 | Howard et al. | |
| 6,752,794 B2 | 6/2004 | Lockwood et al. | |
| 6,755,807 B2 | 6/2004 | Risk et al. | |
| 6,800,074 B2 | 10/2004 | Henley et al. | |
| 6,840,960 B2 | 1/2005 | Bubb | |
| 6,841,715 B2 | 1/2005 | Roberts | |
| 6,855,135 B2 | 2/2005 | Lockwood et al. | |
| 6,856,821 B2 | 2/2005 | Johnson | |
| 6,979,324 B2 | 12/2005 | Bybordi et al. | |
| 7,022,113 B2 | 4/2006 | Lockwood et al. | |
| 7,070,584 B2 | 7/2006 | Johnson et al. | |
| 7,198,046 B1 | 4/2007 | Argenta et al. | |
| 7,216,651 B2 | 5/2007 | Argenta et al. | |
| 7,438,705 B2 | 10/2008 | Karpowicz et al. | |
| 7,532,953 B2 | 5/2009 | Vogel | |
| 7,608,066 B2 | 10/2009 | Vogel | |
| 2001/0031943 A1 * | 10/2001 | Urie | 604/43 |
| 2002/0065494 A1 * | 5/2002 | Lockwood et al. | 604/313 |
| 2003/0187515 A1 | 10/2003 | Hariri et al. | |
| 2003/0212359 A1 | 11/2003 | Butler | |
| 2003/0225355 A1 | 12/2003 | Butler | |
| 2004/0002670 A1 * | 1/2004 | Mothersbaugh et al. | 602/1 |
| 2004/0219133 A1 | 11/2004 | Lyles | |
| 2005/0095723 A1 | 5/2005 | DiTrolio et al. | |
| 2005/0137539 A1 | 6/2005 | Biggie et al. | |
| 2005/0245904 A1 | 11/2005 | Estes et al. | |
| 2006/0025727 A1 | 2/2006 | Boehringer et al. | |
| 2007/0027414 A1 | 2/2007 | Hoffman et al. | |
| 2007/0032763 A1 | 2/2007 | Vogel | |
| 2007/0219532 A1 | 9/2007 | Karpowicz et al. | |
| 2009/0069761 A1 | 3/2009 | Vogel | |

FOREIGN PATENT DOCUMENTS

| | | |
|---|---|---|
| DE | 41 11 122 A1 | 4/1993 |
| DK | 64055 | 10/1945 |
| EP | 0 880 953 A2 | 12/1998 |
| GB | 641061 | 8/1950 |
| GB | 1273342 | 5/1972 |
| SU | 0587941 | 1/1978 |
| SU | 1268175 A1 | 11/1986 |
| WO | WO-90/11795 | 10/1990 |
| WO | WO-91/16030 | 10/1991 |
| WO | WO-92/19313 | 11/1992 |
| WO | WO-92/20299 | 11/1992 |
| WO | WO-96/05873 | 2/1996 |
| WO | WO-01/30422 | 5/2001 |

OTHER PUBLICATIONS

International Search Report for International Application No. PCT/US06/28738 mailed May 10, 2007, 2 pages.

P. Svedman et al, "Treatment of leg ulcers by intermittent irrigation through a felt dressing", IRCS Med. Sci., 13, 489-490 (1985).

P. Svedman, "A Dressing Allowing Continuous Treatment of a Biosurface", IRCS Medical Science: Biomedical Technology; Clinical Medicine; Surgery and Transplantation, 7, 221 (1979).

Egnell Minor, Instruction book, First Edition, 300 7502 [Feb. 1975] (w/ partial English Translation).

Addition to the Users Manual Concerning Overflow Protection concerns all Egnell pumps, dated Feb. 3, 1983 (w/partial English translation).

Sames, C. Patrick, "Sealing of Wounds With Vacuum Drainage", Date unknown, prior to Aug. 8, 2004.

International Preliminary Report on Patentability mailed Feb. 21, 2008 for International Application No. PCT/US2006/028738, International Filing date Jul. 25, 2006.

Office Action mailed May 12, 2008 for U.S. Appl. No. 11/851,941, filed Sep. 7, 2007.

Office Action mailed Dec. 13, 2007 for U.S. Appl. No. 11/851,941, filed Sep. 7, 2007.

Office Action mailed Jul. 9, 2008 for U.S. Appl. No. 11/851,942, filed Sep. 7, 2007.

Office Action mailed Jul. 16, 2008 for U.S. Appl. No. 11/851,944, filed Sep. 7, 2007.

Office Action mailed Jul. 22, 2008 for U.S. Appl. No. 11/851,941, filed Sep. 7, 2007.

Wolthuis et al., "Physiological Effects of Locally applied Reduced Pressure in Man," Physiological Reviews, 54: 566-595, Jul. 1974.

Lundvall et al., "Transmission of externally applied negative pressure of the underlying tissue. A study on the upper arm of man," Acta Physiol Scand, 136: 403-409, accepted Jan. 28, 1989.

Dunlop et al., "Vacuum drainage of groin wounds after vascular surgery: a controlled trial," Br. J. Surg., 77: 562-563 (1990).

Bucalo et al., "Inhibition of cell proliferation by chronic wound fluid," Wound Repair and Regeneration, Miami, 1993, 181-186.

Urschel et al., "The effect of mechanical stress on soft and hard tissue repair; a review," British Journal of Plastic Surgery, 41, 182-186, 1988.

Jeter, K.R. et al. (eds.), "Managing Draining Wounds And Fistulae: New And Established Methods," Chronic Wound Care: Health Management Publications, 1990, pp. 240-246.

Fleischmann, W., Wund Forum Spezial. IHW '94. "Vakuumversiegelung zur Behandlung von Problemwunden," (English translation: Vacuum sealing for Treatment of Problematical Wounds.).

Fleischmann, W. et al., Acta Orthopaedica Belgica. vol. 58, Suppl. I-1992, "Treatment of Bone and Soft Tissue Defects in Infected Nonunion."

Fleischmann, W. et al., Unfall Chirurgie, Springer-Varlag 1993, "Vakuumverseigelung zur Behandlung des Weichteilschadens bei offenen Frakturen."

Valenta, A., American Journal of Nursing, Apr. 1994, "Using the Vacuum Dressing Alternative for Difficult Wounds."

Mulder, G.D. et al. (eds.), Clinicians' Pocket Guide to Chronic Wound Repair, (Spartanburg, SC: Wound Healing Publications), 1991, pp. 54-55.

Morykwas, M. et al., "Use of Negative Pressure to Increase the Rate of Granulation Tissue Formation in Chronic Open Wounds," Extracellular Matrix and Healing, pp. 800, 1993.

Schneider, A. et al., "A New and Reliable Method of Securing Skin Grafts to the Difficult Recipient Bed," Plastic and Reconstructive Surgery, vol. 102(4), Sep. 1998, pp. 1195-1198.

Morykwas, M. et al., "Nonsurgical Modalities to Enhance Healing and Care of Soft Tissue Wounds," Journal of the Southern Orthopaedic Association, vol. 6, No. 4, Winter 1997, pp. 279-288.

Tittle, K. et al., "VariDyne—new standards in postoperative wound drainage," Unfall Chirurgie, 1988, 14(2):104-107.

Genecov, A. et al., "A Controlled Subatmospheric Pressure Dressing Increases the Rate of Skin Graft Donor Site Reepithelialization," Annals of Plastic Surgery, Col. 40, No. 3, Mar. 1998, pp. 219-225.

Morykwas, M. et al., "Vacuum Assisted Closure: A New Method for Wound Control and Treatment: Animal Studies and Basic Foundation"—Annals of Plastic Surgery, vol. 38, No. 6, Jun. 1997.

Argenta, L. et al., "Vacuum-Assisted Closure: A New Method for Wound Control and Treatment: Clinical Experience," Annals of Plastic Surgery, vol. 38, No. 6, Jun. 1997.

Neumann, P. et al., "Gelatin-based sprayable foam as a skin substitute," Journal of Biomedical Materials Research, 1981; vol. 15, pp. 9-18.

Office Action mailed Oct. 17, 2008, for U.S. Appl. No. 11/350,089, filed Feb. 9, 2006.

Office Action mailed Dec. 26, 2008 for U.S. Appl. No. 11/851,944, filed Sep. 7, 2007.

Office Action mailed Jan. 7, 2009 for U.S. Appl. No. 11/851,942, filed Sep. 7, 2007.

Office Action mailed Oct. 7, 2009 for U.S. Appl. No. 11/851,944, filed Sep. 7, 2007.

* cited by examiner

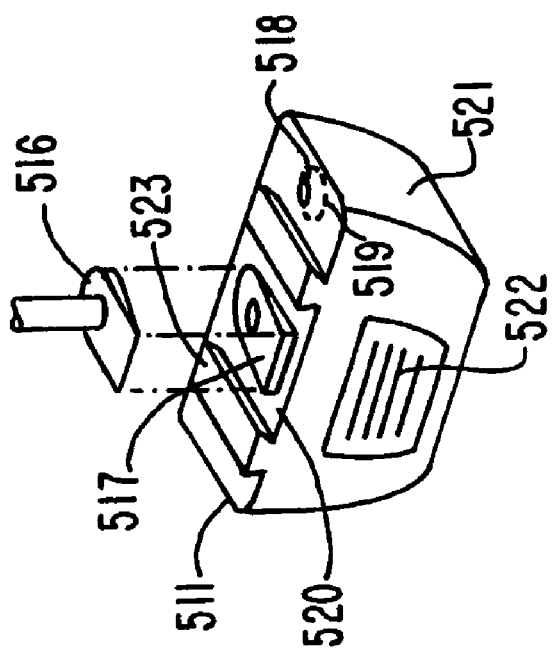
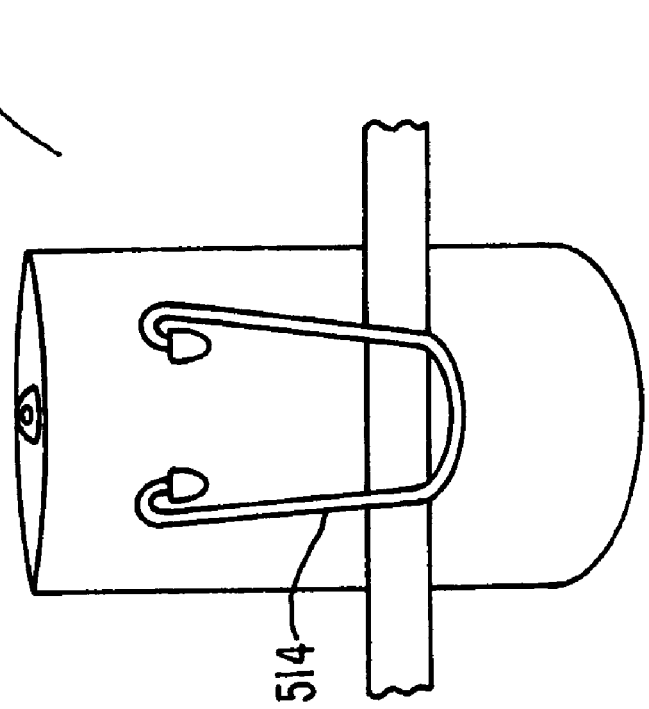

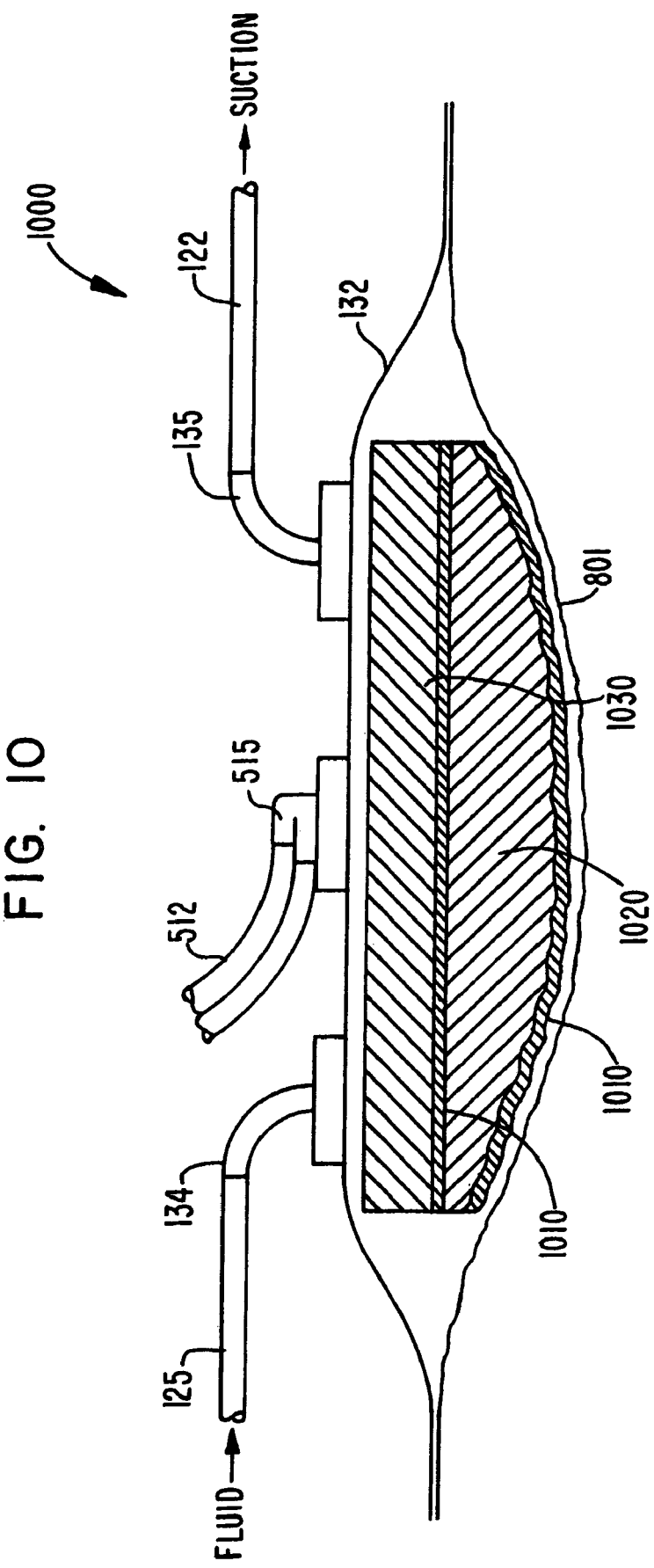

WOUND IRRIGATION DEVICE

CROSS REFERENCE TO RELATED APPLICATION

This application is a Continuation of U.S. patent application Ser. No. 11/198,148, entitled "Wound Irrigation Device," filed Aug 8, 2005, now abandoned, the entirety of which is hereby incorporated by reference.

BACKGROUND

The invention is generally directed to a method and apparatus for the promotion of wound healing. More particularly, the present invention relates to providing fluid irrigation and vacuum drainage of a wound.

Negative pressure wound therapy, also known as vacuum drainage or closed-suction drainage is known. A vacuum source is connected to a semi-occluded or occluded wound dressing. Various porous dressings comprising gauze, felts, foams, beads and/or fibers can be used in conjunction with an occlusive semi-permeable cover and a controlled vacuum source.

In addition to using negative pressure wound therapy, many devices employ concomitant wound irrigation. For example, a known wound healing apparatus includes a porous dressing made of polyurethane foam placed adjacent a wound and covered by a semi-permeable and flexible plastic sheet. The dressing further includes fluid supply and fluid drainage connections in communication with the cavity formed by the cover and foam. The fluid supply is connected to a fluid source that can include an aqueous topical antibiotic solution or isotonic saline for use in providing therapy to the wound. The fluid drainage can be connected to a vacuum source where fluid can be removed from the cavity and subatmospheric pressures can be maintained inside the cavity. The wound irrigation apparatus, although able to provide efficacious therapy, is somewhat cumbersome, difficult to use, and generally impractical. Such a device does not address various factors concerning patients, specifically ease of use, portability and the ability to provide therapy with a minimum amount of unwanted mechanical noise.

Other devices use vacuum sealing of wound dressings consisting of polyvinyl alcohol foam cut to size and stapled to the margins of the wound. The dressings are covered by a semi-permeable membrane while suction and fluid connections are provided by small plastic tubes introduced subcutaneously into the cavity formed by the foam and cover. Such devices alternate in time between vacuum drainage and the introduction of aqueous medicaments to the wound site. Such devices also fail to address portability, ease of use and noise reduction.

SUMMARY OF THE INVENTION

One embodiment of the invention is directed to a wound irrigation system: using an electromechanical vacuum apparatus that includes a microprocessor-based device having stored thereon software configured to control the electromechanical vacuum apparatus. A first vacuum pump is electrically associated with the microprocessor and is capable of generating a vacuum. An optional second vacuum pump is electrically associated with the microprocessor and is capable of maintaining a predetermined vacuum level. A first electronic vacuum-pressure sensor is operably associated with the vacuum pump(s) and said microprocessor for monitoring vacuum level. A fluid-tight collection canister includes an integrated barrier to prevent contents from escaping the canister. Canulated tubing is associated with the canister and vacuum pump(s) for communicating vacuum pressure therefrom. A second electronic vacuum-pressure sensor is operably associated with the canister and the microprocessor for monitoring canister vacuum. A dressing includes of a porous material and semi-permeable flexible cover, Canulated tubing is associated with the dressing and the canister to communicate vacuum pressure therefrom. An irrigation vessel contains a fluid to be used in irrigating the wound. Canulated tubing is associated with the irrigation vessel and the dressing to communicate fluid thereto. The electromechanical vacuum apparatus has an integrated compartment that can hold the irrigation vessel. The electromechanical vacuum apparatus may optionally include a device for regulating the quantity of fluid flowing from said irrigation vessel to said dressing. The electromechanical vacuum apparatus may include batteries enabling portable operation thereof.

An embodiment of the invention includes a method for improving the generation and control of a therapeutic vacuum. In this embodiment, a multi-modal algorithm monitors pressure signals from a first electronic vacuum-pressure sensor associated with a vacuum pump and capable of measuring the output pressure from the pump. The algorithm further monitors pressure signals from a second electronic vacuum-pressure sensor associated with a collection canister and capable of measuring the subatmospheric pressure inside the canister. The canister is connected to the vacuum pump by a canulated tube that communicates subatmospheric pressure therefrom. The canister is connected to a suitable dressing by a canulated tube that communicates subatmospheric pressure thereto. At the start of therapy, both the first and second electronic vacuum-pressure sensors indicate the system is equilibrated at atmospheric pressure. A first-mode control algorithm is employed to remove rapidly the air in the canister and dressing, and thus create a vacuum. The first-mode implemented by the control algorithm is subsequently referred to herein as the "draw down" mode. Once the subatmospheric pressure in the canister and dressing have reached a preset threshold as indicated by the first and second electronic vacuum-pressure sensors respectively, the algorithm employs a second-mode that maintains the desired level of subatmospheric pressure in both the canister and the dressing for the duration of the therapy. The second-mode implemented by the control algorithm is subsequently referred to herein as the "maintenance" mode. The second-mode control algorithm is configured to operate the vacuum pump at a reduced speed thus minimizing unwanted mechanical noise. In an alternative embodiment, a second vacuum pump can be used for the maintenance mode, which has a reduced capacity, is smaller, and produces significantly lower levels of unwanted mechanical noise. The second-mode control algorithm is configured to permit the maintenance of vacuum in the presence of small leaks, which invariably occur at the various system interfaces and connection points. The method can be performed by, for example, a microprocessor-based device.

In another embodiment application-specific dressings are configured according to the individual needs of varying wound types. A myriad of new materials that broadly fall into the categories of antibacterial, biodegradable, and bioactive can be used to create highly efficacious wound dressings. For a material to function with a wound irrigation and vacuum drainage system, the dressing composition can be porous enough to permit the uniform distribution of subatmospheric pressure throughout the dressing and subsequently to facilitate the removal of fluids therethrough. In addition, the dressings possess various mechanical properties that can create the proper macro-strain and micro-strain on the wound bed believed to contribute to the production of growth factors and other cytokines that promote wound healing. Accordingly, some embodiments include several dressing arrangements that use, for example, the aforementioned materials to produce dressings for specific wound types.

BRIEF DESCRIPTION OF THE DRAWINGS

FIGS. 5A-5C are illustrations of a device according to an embodiment of the invention for providing portable wound irrigation and vacuum drainage.

FIG. 10 is an illustration of an application-specific dressing according to an embodiment of the invention incorporating bioactive materials in the dressing.

DETAILED DESCRIPTION

Although those of ordinary skill in the art will readily recognize many alternative embodiments, especially in light of the illustrations provided herein, this detailed description is of an embodiment of the invention, the scope of which is defined only by the claims appended hereto.

Figure 1:
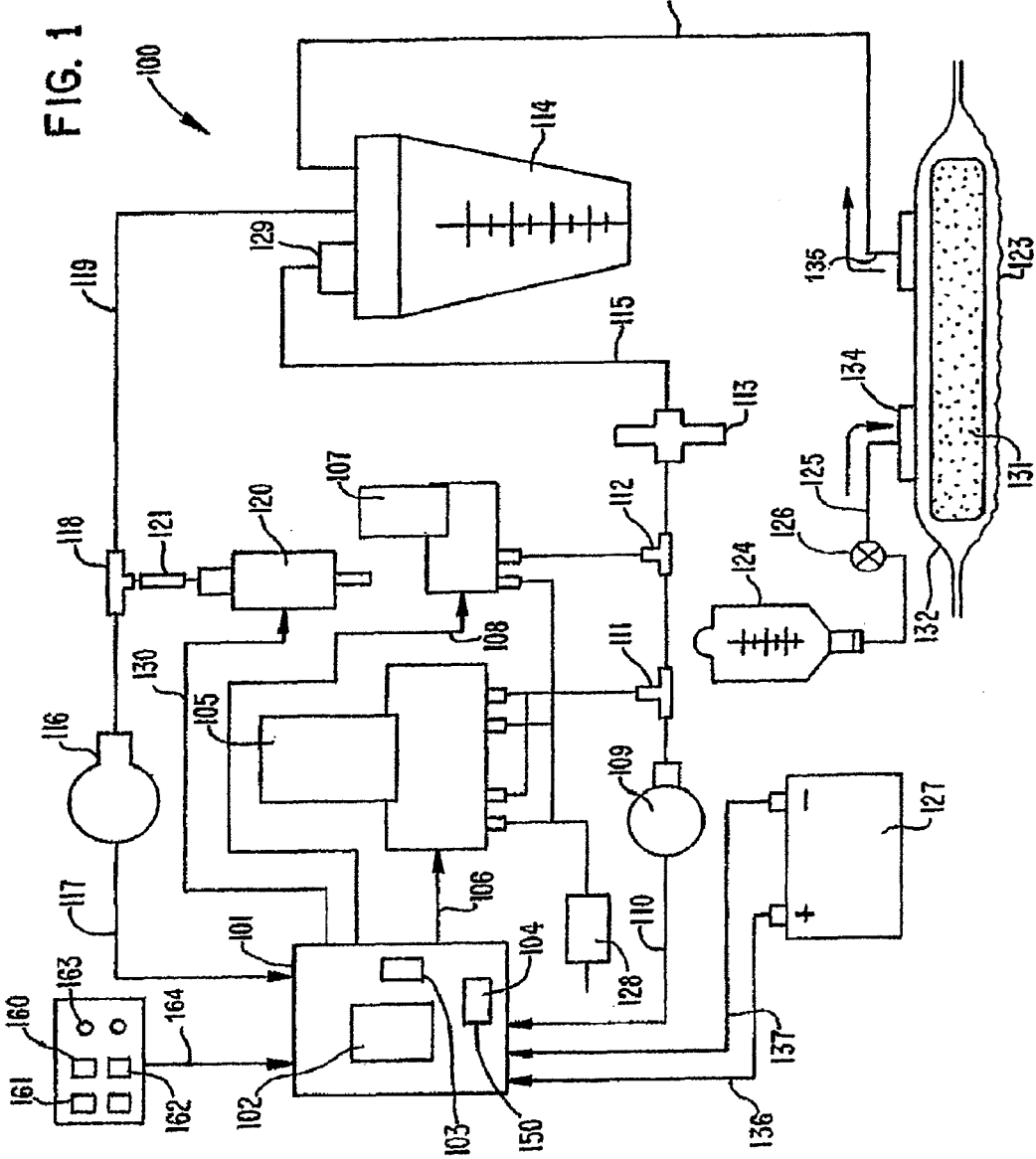
FIG. 1 is a schematic block diagram of an embodiment of the invention for providing wound irrigation and vacuum drainage.

As illustrated in FIG. 1, a wound irrigation and vacuum drainage system is referred to by the numeral 100 and generally includes a microcontroller 101 having an embedded microprocessor 102, Random Access Memory (RAM) 103 and Read Only Memory (ROM) 104. ROM 104 contains the programming instructions for a control algorithm 150 (see FIG. 2). ROM 104 is non-volatile and retains its programming when the power is terminated. RAM 103 is utilized by the control algorithm for storing variables such as pressure measurements, alarm counts and the like, which the control algorithm 150 uses while generating and maintaining the vacuum. A membrane keypad and display 160 is electrically associated with microcontroller 101 through communication cable 164. Membrane switches 161 provide power control and membrane switches 162 are used to preset the desired vacuum levels. Light emitting diodes (LEDs) 163 are provided to indicate alarm conditions associated with canister fluid level and dressing leaks.

Microcontroller 101 is electrically associated with, and controls the operation of, a first vacuum pump 105 and an optional second vacuum pump 107 through electrical cables 106 and 108 respectively. First vacuum pump 105 and optional second vacuum pump 107 can be one of many types including, for example, the pumps sold under the trademarks Hargraves® and Thomas®. Vacuum pumps 105 and 107 can use, for example, a reciprocating diaphragm or piston to create vacuum and are typically powered by a D.C. motor that can also optionally use a brushless commutator for increased reliability and longevity. Vacuum pumps 105 and 107 are pneumatically associated with an exudate collection canister 114 through a single-lumen tube 115. In one embodiment, canister 114 has a volume which does not exceed 1000 ml. This can prevent accidental exsanguination of a patient in the event hemostasis has not yet been achieved at the woundsite. Canister 114 can be of a custom design or one available off-the-shelf and sold under the trademark Medi-VAC®. In addition, a fluid barrier 129 is associated with canister 114 and is configured to prevent fluids collected in canister 114 from escaping into tubing 115 and fouling the vacuum return path. Barrier 129 can be of a mechanical float design or may have one or more membranes of hydrophobic material such as those available under the trademark GoreTex™. A secondary barrier 113 using a hydrophobic membrane is inserted inline with pneumatic tubing 115 to prevent fluid ingress into the system in the event barrier 129 fails to operate as intended. Pneumatic tubing 115 connects to first vacuum pump 105 and optional second vacuum pump 107 through "T" connectors 111 and 112 respectively.

Vacuum-pressure sensor 109 is pneumatically associated with first vacuum pump 105 and optional vacuum pump 107 and electrically associated with microcontroller 101 through electrical cable 110. Pressure sensor 109 provides a vacuum-pressure signal to the microprocessor 102 enabling control algorithm 150 to monitor vacuum pressure at the outlet of the vacuum pumps 105 and 107. An acoustic muffler 128 is pneumatically associated with the exhaust ports of vacuum pumps 105 and 107 and is configured to reduce induction noise produced by the pumps during operation. In normal operation of irrigation system 100, first vacuum pump 105 is used to generate the initial or "draw-down" vacuum while optional second vacuum pump 107 can be used to maintain a desired vacuum within the system compensating for any leaks or pressure fluctuations. Vacuum pump 107 can be smaller and quieter than vacuum pump 105 providing a means to maintain desired pressure without disturbing the patient.

A battery 127 is optionally provided to permit portable operation of the wound irrigation system 100. Battery 127, which can be Nickel-Metal-Hydride (NiMH), Nickel—Cadmium, (NiCd) or their equivalent, is electrically associated with microcontroller 101 through electrical cables 136 and 137. Battery 127 is charged by circuits related with microcontroller 101 while an external source of power is available. When an external source of power is not available and the unit is to operate in a portable mode, battery 127 supplies power to the wound irrigation system 100.

A second pressure sensor 116 is pneumatically associated with canister 114 through a single-lumen tube 119. Pressure sensor 116 is also electrically associated with microcontroller 101 and provides a vacuum-pressure signal to microprocessor 102 enabling control algorithm 150 to monitor vacuum pressure inside canister 114 and dressing 123. A "T" connector 118 is connected pneumatic tube 119 to pressure sensor 116 and a vacuum-pressure relief solenoid 120 configured to relieve pressure in the canister 114 and dressing 123 in the event of an alarm condition, or if power is turned off. Solenoid 120, can be, for example, one available under the trademark Pneutronics®; Solenoid 120 is electrically associated with, and controlled by, microprocessor 101 through electrical cable 130. Solenoid 120 is configured to vent vacuum pressure to atmosphere when the electrical coil is de-energized as would be the case if the power is turned off. An orifice restrictor 121 is provided inline with solenoid 120 and pneumatic tube 119 to regulate the rate at which vacuum is relieved to atmospheric pressure when solenoid 120 is de-energized. Orifice restrictor 121 is, for example, available under the trademark AirLogic®.

A wound dressing 123 includes a sterile porous substrate 131, which can be a polyurethane foam, polyvinyl alcohol foam, gauze, felt or other suitable material, a semi-permeable adhesive cover 132 such as that sold under the trademark Avery Denison®, an inlet port 134 and a suction port 135. Dressing substrate 131 is configured to distribute evenly the vacuum pressure throughout the entire wound bed and has mechanical properties suitable for promoting the formation of granular tissue. In addition, when vacuum is applied to dressing 123, substrate 131 creates micro- and macro-strain at the cellular level of the wound stimulating the production of various growth factors and other cytokines and promoting cell proliferation. Dressing 123 is fluidically associated with canister 114 through a single-lumen tube 122. The vacuum pressure in the cavity formed by substrate 131 of dressing 123 is largely the same as the vacuum pressure inside canister 114 minus the weight of any standing fluid inside tubing 122. A fluid vessel 124, which can be a standard I.V. bag, contains medicinal fluids such as aqueous topical antibiotics, physiologic bleaches, or isotonic saline. Fluid vessel 124 is removably connected to dressing 132 though port 134 and single-lumen tube 125. An optional flow control device 126 can be placed inline with tubing 125 to permit accurate regulation of the fluid flow from vessel 124 to dressing 123. In normal operation, continuous woundsite irrigation is provided as treatment fluids move from vessel 124 through dressing 123 and into collection canister 114. This continuous irrigation keeps the wound clean and helps to manage infection. In addition, effluent produced at the woundsite and collected by substrate 131 will be removed to canister 114 when the system is under vacuum.

Figure 2:
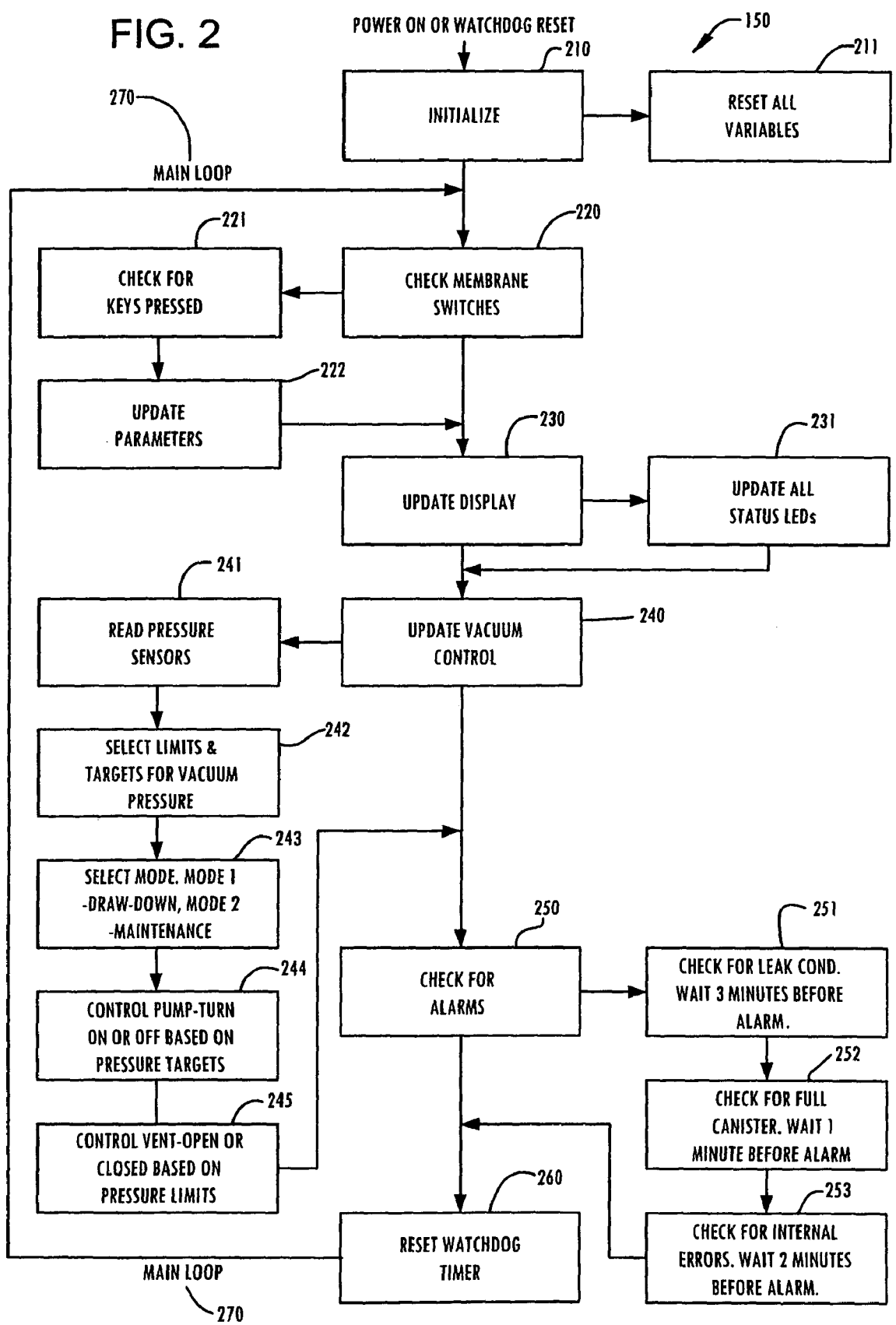
FIG. 2 is a flow diagram for a method according to an embodiment of the invention.

Referring to FIG. 2, an example of the general processing steps of algorithm 150 are illustrated. Algorithm 150 includes a continuously executing "Main Loop" 270 having six functional software modules: Initialization module 210, Check Membrane Switches module 220, Update Display module 230, Update Vacuum Control module 240, Check for Alarms (full canister, leak, internal) module 250, and Reset Watchdog Timer module 260.

At initialization step 210, all the variables associated with the operation of the control algorithm 150 are reset. The initialization step 210 can execute, for example, when power is applied to the system. The variables that can be reset include, for example, alarm flags, alarm time counters, pressure targets, pressure limits and internal variables used for storing mathematical calculations.

At step 220, the algorithm 150 checks for any user input via the membrane keypad. At step 221, any keypresses are checked. At step 222, all therapy-related patameters are updated. For example, a user may press the vacuum-level-preset switch 162 which would be detected at step 221. The new target pressure selected by the user would then be stored as a therapy parameter in step 222. If no keys are pressed, or once the therapy parameters have been updated subsequent any key press, algorithm 150 updates the display at step 230.

At step 230, all status LED's are updated including any alarm indications that may have been identified in the previous pass through the main loop 270.

At step 240, algorithm 150 monitors and updates control of the vacuum pump(s) 105 and 107, and vent solenoid 120. At step 241, the actual pressure at the pump(s) 105 and 107 and the canister 114 is read via electronic vacuum-pressure sensors 109 and 116, respectively. These analog readings are digitized and stored for use on the next pass through main loop 270. At step 242, vacuum limits and targets are selected based on the pre-determined therapy parameters identified in step 220. At step 243, a decision is made regarding in which mode the pump(s) will be operated. If the first-mode is selected at step 243, algorithm 150 will operate vacuum pump 105 at full-power minimizing the time to remove the air from canister 114 and dressing 132. If the second-mode is selected at step 243, algorithm 150 will operate vacuum pump 105 at partial-power providing just enough airflow to keep up with any leaks in the system as described in detail earlier. In this mode, pump 105 operates very quietly and would not disturb the patient. Alternatively, and described in more detail hereinbelow, an optional pump 107 can be utilized in conjunction with pump 105 during second-mode operation. In this embodiment, pump 107 is smaller and quieter than pump 105 and has reduced airflow capacity. Pump 107 is configured to provide just enough airflow to compensate for system leaks or other loss of vacuum.

Once the mode is selected at step 243, algorithm 150 produces electronic control signals that turn the vacuum pump(s) 105 and 107 on or off at step 244. In addition, and as described in detail hereinabove, a solenoid valve 120 vents vacuum pressure to atmosphere when power is terminated, or in the event vacuum pressure exceeds the preset limits established at step 242. At step 245, the control signals are provided and are based on comparisons between actual pressure, target pressure and the preset high-pressure limit. Mode determination, vacuum pump control, and vent control are all based on comparisons between the pre-selected target pressure levels and actual pressure readings obtained at steps 241 and 242, respectively.

After pressure adjustments are made and the actual pressure readings obtained at step 240, the algorithm 150 checks for alarm conditions at step 250. At step 251, leak conditions, which are readily identified by analyzing the readings from pressure sensors 109 and 116, are identified. If a leak condition is detected at step 251, the algorithm 150 waits three minutes before flagging the leak alarm and alerting the user at step 230 during the next pass through main loop 270. At step 252, a full canister condition is checked, again easily identified by analyzing the readings from pressure sensors 109 and 116. If a full canister condition is detected at step 252, the algorithm 150 waits one minute before flagging the full canister alarm and alerting the user at step 230 during the next pass through main loop 270. At step 253, the readings from pressure sensors 109 and 116 are examined to determine if any internal errors exist. An internal error would occur if one pressure sensor indicated a pressure reading, for example, 30 mmHg higher or lower than the other sensor. Again, if the internal error condition is detected at step 253, the algorithm 150 waits two minutes before flagging the internal error alarm and alerting the user at step 230 during the next pass through main loop 270.

After completion of steps 220, 230, 240 and 250, algorithm 150 will reset the watchdog timer at step 260. The watchdog timer is provided as a safety feature in the event of an unanticipated software glitch and is incorporated within embedded microprocessor 102. In the event control algorithm 150 "locks up", main loop 270 would no longer function. When main loop 270 ceases to function, the hardware watchdog timer would not be reset at step 260 and would therefore timeout. Once the watchdog timer has timed-out, it will automatically reset embedded microprocessor 102 and algorithm 150 will re-initialize all variables and parameters at step 210. Subsequent to the re-initialization, algorithm 150 would again sequentially execute the modules as described above via main loop 270.

Figure 3:
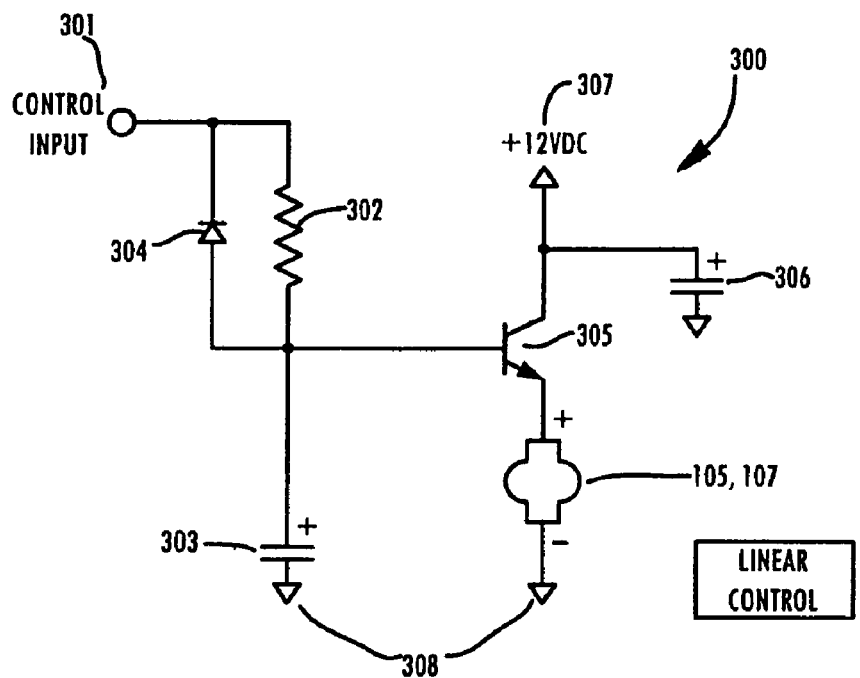
FIG. 3 is an illustration of a maintenance-mode control circuit according to an embodiment of the invention.

Referring now particularly to FIG. 3, an example of a linear control circuit associated with vacuum pump(s) 105 and 107 includes a control input 301, which is a digital signal provided by microcontroller 101. Digital control input 301 is associated with the second-mode described above. When digital control input 301 is in its low or off state, diode 304 becomes forward biased and subsequently discharges capacitor 303. After a short period of time, the voltage across capacitor 303 trends towards zero and the capacitor is substantially fully discharged. When digital control input 301 is in its high or on state, diode 304 becomes reverse biased and is effectively removed from the circuit. In this case, with said second-mode activated, resistor 302, which is in series with capacitor 303, will begin to charge capacitor 303 at a rate determined by the values of both components and proportional to 1/R*C. After approximately 1/R*C seconds have elapsed, capacitor 303 becomes fully charged and no additional current will flow through resistor 302. The voltage across capacitor 303 will be approximately equal to the magnitude of the digital control input 301 voltage. The junction of resistor 302 and capacitor 303 is connected to the base terminal of an NPN bi-junction transistor 305. Transistor 305 can be, for example, a TIP-32C. Transistor 305 is configured as an emitter follower and in this arrangement will provide current amplification. The positive terminal of vacuum pump(s) 105 and 107 is connected to the emitter terminal of transistor 305 while the collector terminal of transistor 305 is connected directly to the 12-volt power supply 307. An additional capacitor 306 is provided to prevent unwanted transients on the power supply caused by the inductive loading of vacuum pump(s) 105 and 107. The negative terminal of vacuum pump(s) 105 and 107 and the negative terminal of capacitor 303 are connected to the common ground reference point 308.

When the digital control input 301 transitions from its low-to-high state, the voltage across capacitor 303 begins to ramp-up slowly until reaching a maximum 1/R*C seconds later. Because of the configuration of transistor 305, the voltage rise at the emitter terminal will mirror the voltage rise at the base terminal, thus the voltage supplied to vacuum pump (s) 105 and 107 will also slowly ramp-up until reaching a maximum 1/R*C seconds later. As the voltage supplied to the pump(s) increases, the pump(s) will operate faster and thus produce more outflow and increased vacuum. Since the time constant is selectable by choosing appropriate values for resistor 302 and capacitor 303, the rate at which the pumps begin to increase speed can be pre-selected and can permit operation at a slower and quieter speed for an extended period of time. As the pump(s) 105 and 107 begin to increase their outflow, vacuum in the system 100 is increased. This increase is measured by algorithm 150, which subsequently changes the state of digital control input 301 in response thereto. As described in detail above, once target pressure has been re-established, the pump(s) 105 and 107 will be shut off. As the digital control input 301 transitions from its high-to-low state after target pressure is met, diode 304 rapidly discharges capacitor 303 as described earlier, and the voltage supplied to pump(s) 105 and 107 is effectively removed turning the pump (s) off.

Figure 4:
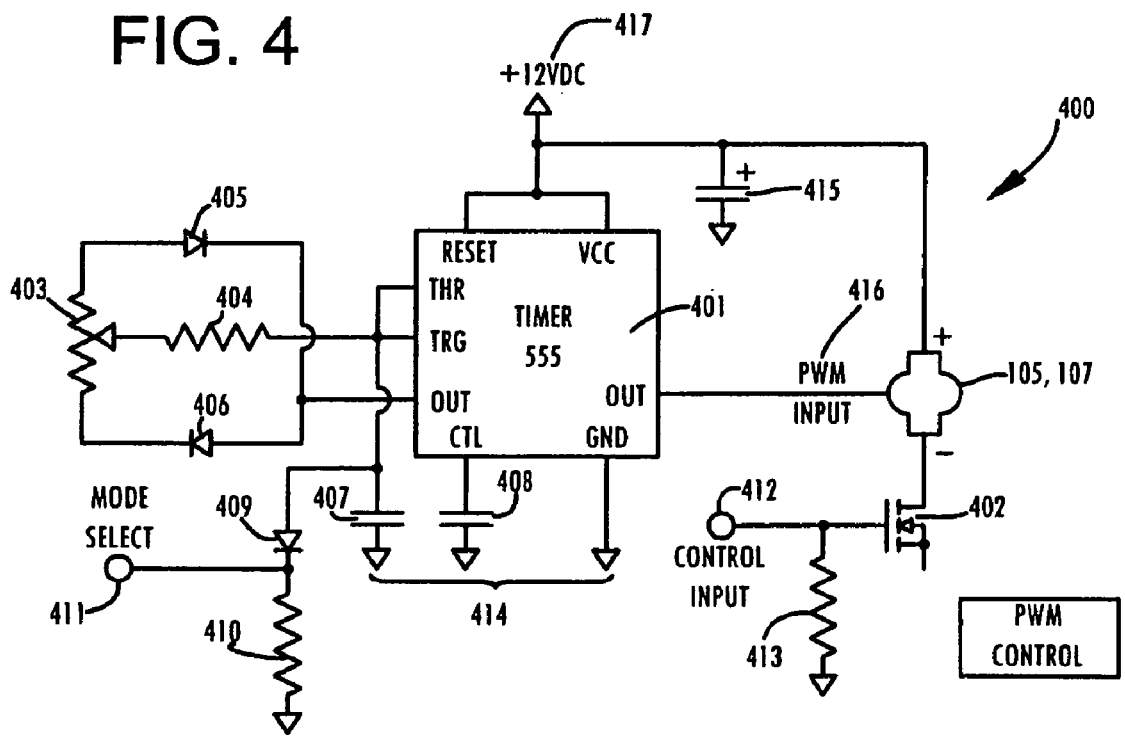
FIG. 4 is an illustration of a maintenance-mode control circuit according to another embodiment of the present invention.

Referring now particularly to FIG. 4, an example of a Pulse Width Modulation (PWM) control circuit 400 associated with vacuum pump(s) 105 and 107 includes an astable multivibrator circuit 401 configured with a duty-cycle that can be varied from approximately 10 to 90 percent. Multivibrator circuit 401 can be, for example, an LM555, and is referred to further herein as "Timer" 401. A 12-volt power supply 417 provides electrical power to timer 401 and vacuum pump(s) 105 and 107. Capacitor 414 is connected between the power supply 417 and the common ground point 414. Capacitor 414 functions to remove transients from the power supply 417 due to inductive loading produced by the operation of pump(s) 105 and 107. In some embodiments of the invention, vacuum pump(s) 105 and 107 have three terminals—a positive and negative terminal for power, and a third terminal 416 that is the PWM control input. The positive terminal of pump(s) 105 and 107 connects to the power supply 417. The negative terminal connects to the drain lead of a MOSFET 402, such as, for example, an IRF510, commonly available and sold under the trademark International Rectifier®. The source lead of MOSFET 402 connects to the common ground point 414. MOSFET 402 switches the power on and off to pump(s) 105 and 107 in response to a control input 412. The signal from control input 412 is provided by microcontroller 101 and acts in conjunction with mode-select signal 411. A resistor 413 is connected between the gate of MOSFET 402 and common ground point 414 and provides ground reference for the gate of MOSFET 402 and drive impedance for control input 412.

Timer 401 has several peripheral components that control the frequency of operation and the duty-cycle of the output waveform. Capacitor 408 stabilizes an internal voltage reference and keeps the output frequency constant. Diodes 405 and 406 charge and discharge capacitor 407 through resistors 403 and 404. Resistor 404 and capacitor 407 determine the output frequency while variable resistor 403 determines the duty-cycle and can be adjusted from 10 to 90 percent. Typically the output frequency would be between 10 kilohertz and 20 kilohertz to minimize switching noise as these frequencies are above the nominal range of human hearing. The output of timer 401 is used as the PWM input 416 and varies the motor speed of pump(s) 105 and 107 in proportion to duty-cycle. A high duty-cycle causes the pump motor to run faster and produce greater outflow while a low duty-cycle causes the pump motor to run slower and quieter with an associated reduction in outflow.

A digital-mode signal from mode select 411 indicating the second mode, which enables selection of said first-mode or said second-mode, is provided to capacitor 407 through diode 409. When the mode-select signal from mode select 411 transitions from a high to low state, diode 409 is forward biased and rapidly discharges capacitor 407. When capacitor 407 is in its discharged state, the PWM signal 416 generated by timer 401 is forced high. A constant, high PWM is equivalent to a 100% duty-cycle and thus pump(s) 105 and 107 run at maximum in this configuration. As mode-select signal from mode select 411 transitions from a low to high state, diode 409 is reverse biased and therefore effectively removed from the circuit. Timer 401 then operates in an astable mode producing a reduced duty-cycle PWM signal 416. Resistor 410 is connected between mode select input 411 and common ground point 414 to provide drive impedance for microcontroller 101.

When control algorithm 150 determines that the first-mode (draw-down) is required such as when the system is initializing and drawing-down the dressing, mode select signal from mode select 411 will be in a low state while control-input signal from control input 412 will be in a high state. This configuration will cause vacuum pump(s) 105 and 107 to produce the greatest amount of outflow. Likewise when control algorithm 150 determines that said second-mode (maintenance) is required such as when the measured therapeutic vacuum level dips below the predetermined low-limit, mode-select signal from mode select 411 will be in a high state while control-input signal from control input 412 will be in a high state. This configuration will cause vacuum pump(s) 105 and 107 to operate at a slower speed producing reduced outflow and reduced unwanted mechanical noise while simultaneously restoring therapeutic vacuum to the target level. If control-input signal from control input 412 is in a low state, the pump(s) are disabled and do not operate at all. This acts as a safety feature in the event of a component failure that causes pump(s) 105 and 107 to latch in an on-state.

Figure 5A:
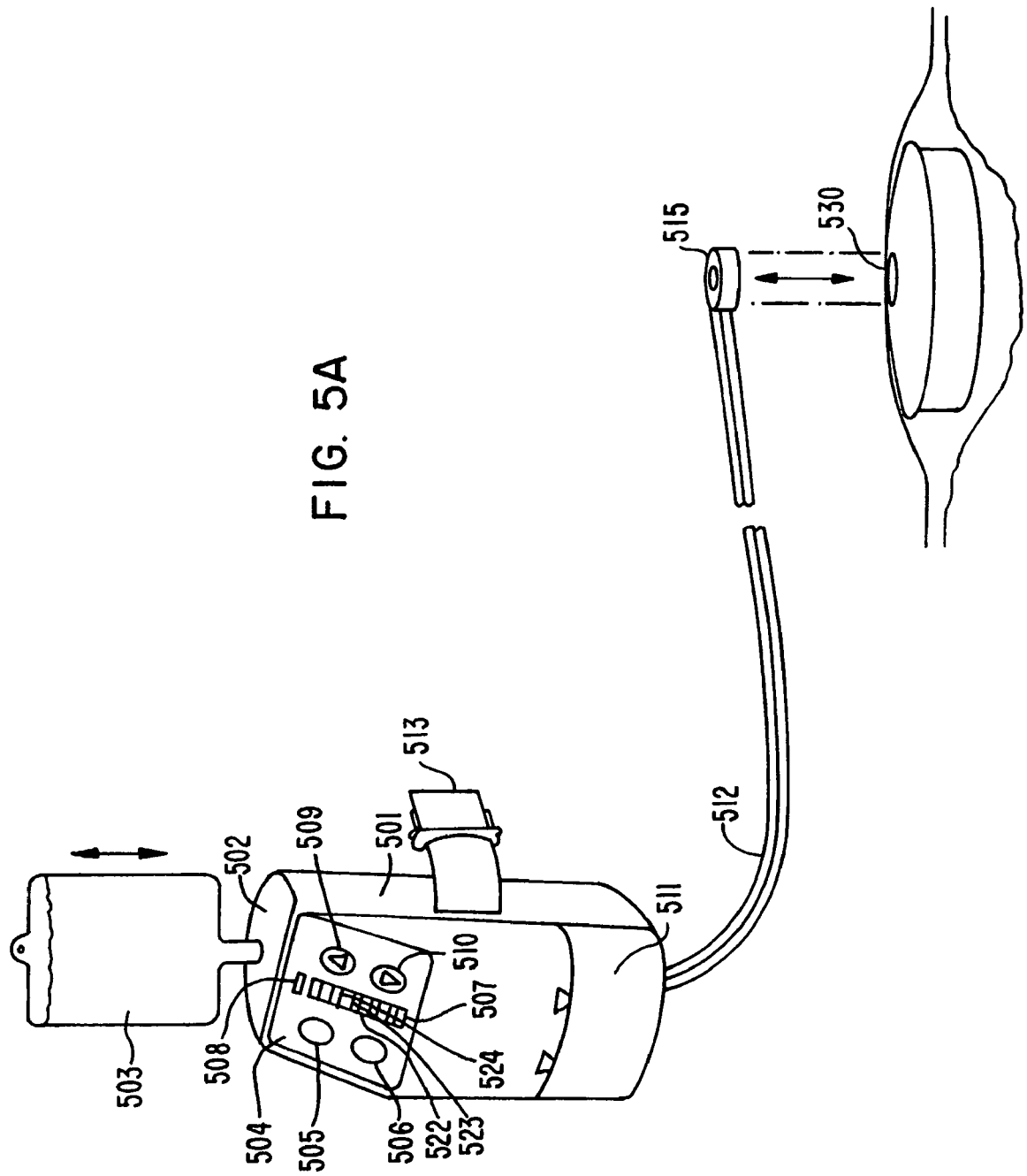

Referring now particularly to FIG. 5A, another embodiment of a portable system 500 for providing therapeutic wound irrigation and vacuum drainage is illustrated. System 500 includes a self-contained plastic housing 501 configured to be worn around the waist or carried in a pouch over the shoulder for patients who are ambulatory, and hung from the footboard or headboard of a bed for patients who are non-ambulatory. A membrane keypad and display 504 is provided to enable the adjustment of therapeutic parameters and to turn the unit on and off. Depressing membrane switch 505 will turn the power to system 500 on while depressing membrane switch 506 will turn the power off. Membrane switch 509 adjusts the target therapeutic pressure up and likewise membrane switch 510 adjusts the target therapeutic pressure down. In some embodiments of the invention, system 500 has three pressure settings LOW, MEDIUM and HIGH which generally correspond to, for example, 70 mmHg, 120 mmHg and 150 mmHg, respectively. Although these three pressure settings are provided by way of example, they are not intended to be limiting because other pressures can be utilized for wound-type specific applications. Membrane LEDs LOW 522, MEDIUM 523 and HIGH 524, indicate the current target therapeutic setting of the unit. LED 507 indicates a leak alarm and LED 508 indicates a full-canister alarm. When either alarm condition is detected, these LEDs will light in conjunction with an audible chime. Housing 501 incorporates a compartment 502 that is configured in such a way as to receive and store a standard IV bag 503. IV bag 503 may contain an aqueous topical wound treatment fluid that is utilized by system 500 to provide continuous irrigation. In some embodiments, the wound treatment fluid can be introduced directly into compartment 502. Additionally, the IV bag 503 can be externally coupled to the device. As shown in FIG. 5B, a belt clip 514 is provided for attaching to a patient's belt and an optional waist strap or shoulder strap is provided for patient's who do not wear belts.

As shown in FIG. 5C, an exudate collection canister 511 comprises a vacuum-sealing means 517 and associated hydrophobic filter 520 (not shown), vacuum sensor port 518 and associated hydrophobic filter 519 (not shown), frosted translucent body 521, clear graduated measurement window 522, locking means 523 and multilumen tubing 512. Collection canister 511 typically has a volume less than 1000 ml to prevent accidental exsanguination of a patient. Vacuum sealing means 517 mates with a corresponding sealing means 516 that is incorporated in housing 501. In addition, locking means 523 has corresponding mating components within said housing. Hydrophobic filters 519 and 520 can be, for example, those sold under the trademark GoreTex® and are ensured the contents of canister 511 do not inadvertently ingress housing 501 and subsequently cause contamination of the therapy device 500. Vacuum sensor port 518 enables microcontroller 101 to measure the pressure within the canister 511 as a proxy for the therapeutic vacuum pressure under the dressing 131. Multilumen tubing 512 provides one conduit for the irrigation fluid to travel to dressing 131 and another conduit for the vacuum drainage. Thus, IV bag 503, tubing 512, dressing 131 and canister 511 provide a closed fluid pathway. In this embodiment, canister 511 would be single-use disposable and may be filled with a gelling substance to enable the contents to solidify prior to disposal. Gelling agents are available, for example, under the trademark Isolyzer®.

As shown in FIG. 5A, at the termination of tubing 512, a self-adhesive dressing connector 515 is provided for attaching the tubing to drape 132 with substantially air-tight seal. Dressing connector 515 can have an annular pressure-sensitive adhesive ring with a release liner that is removed prior to application. In actual use, a small hole 530 can be cut in drape 132 and dressing connector 515 would be positioned in alignment with said hole. This enables irrigation fluid to both enter and leave the dressing through a single port. In an alternative embodiment, tube 512 bifurcates at the terminus and connects to two dressing connectors 515 which allow the irrigation port to be physically separated from the vacuum drainage port thus forcing irrigation fluid to flow though the entire length of the dressing if it is so desired.

Figure 6:
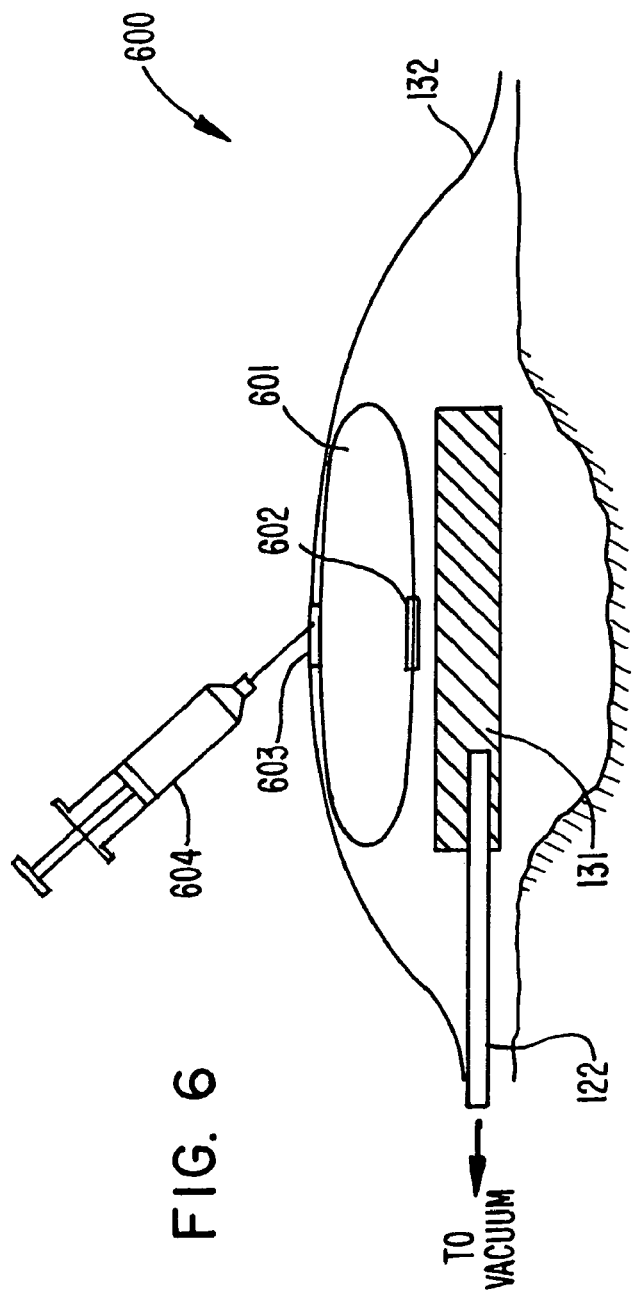
FIG. 6 is a second illustration of a device according to an embodiment of the invention for providing portable wound irrigation and vacuum drainage.

Referring now to FIG. 6, and according to a further embodiment of the invention, a dressing system 600 for providing therapeutic wound irrigation and vacuum drainage is illustrated. Dressing system 600 includes a sterile porous substrate 131, which can be fabricated from polyurethane foam, polyvinyl alcohol foam, gauze, felt or other suitable material; a semi-permeable adhesive cover 132 such as that sold under the trademark Avery Denison®; a single lumen drainage tube 122 for the application of vacuum and removal of fluids from the woundsite; and a pliable fluid vessel 601 situated between the semi-permeable cover 132 and the porous substrate 131. Fluid vessel 601 comprises a self-sealing needle port 603 situated on the superior aspect of the vessel and a regulated drip port 602 situated on the inferior aspect of the vessel. Needle port 603, permits the introduction of a hypodermic needle 604 for the administration of aqueous topical wound treatment fluids. These aqueous topical fluids can include antibiotics such as Bacitracin or Sulfamide-Acetate; physiologic bleach such as Chlorpactin or Dakins solution; and antiseptics such as Lavasept or Octenisept. Regulated drip port 602 permits fluid within vessel 601 to egress slowly and continuously into porous substrate 131 whereupon the therapeutic benefits can be imparted to the woundsite. Single-lumen drainage tube 122 provides enough vacuum to keep the dressing 600 at sub-atmospheric pressure and to remove fluids, which include the irrigation fluid and wound exudate. The advantage of dressing system 600 is the incorporation into the dressing of vessel 601 thus eliminating the need for an external fluid vessel and associated tubing and connectors making the dressing more user friendly for patient and clinician alike.

In normal clinical use, dressing 600 is applied to the wound site by first cutting porous substrate 131 to fit the margins of the wound. Next, semi-permeable drape 132 with integrated (and empty) fluid vessel 601 is attached positioning drip port 602 central to the porous substrate 131. Once the drape 132 is properly sealed around the periwound, a properly prepared hypodermic needle 604 can be inserted in self-sealing needle port 603, and fluid vessel 601 subsequently can fill with the desired aqueous topical wound treatment solution.

Figure 7:
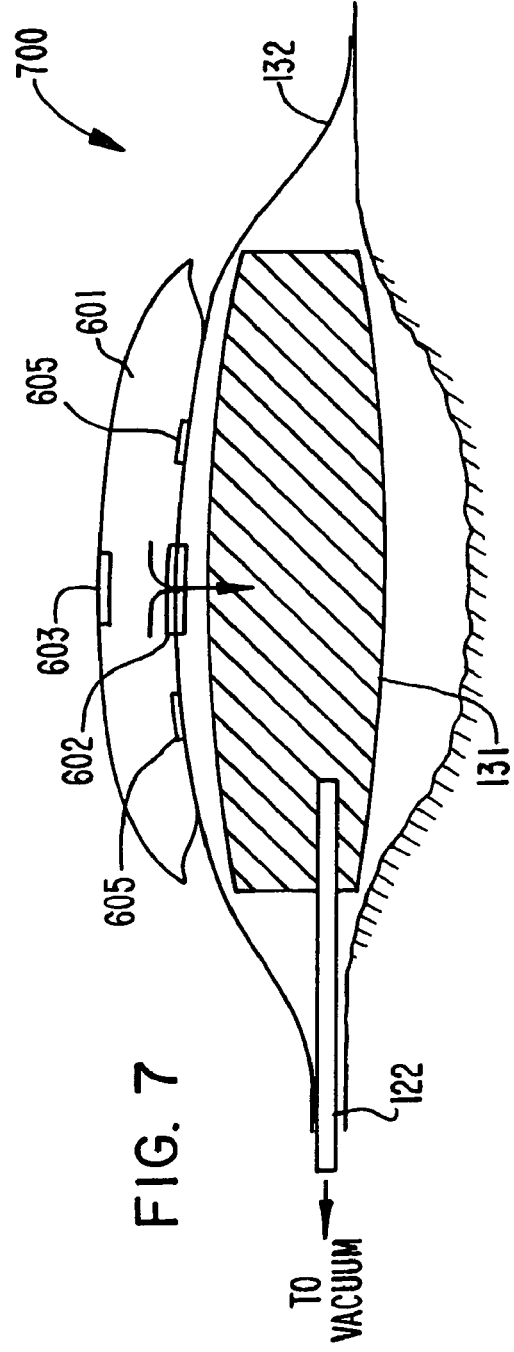
FIG. 7 is a third illustration of a device according to an embodiment of the invention for providing portable wound irrigation and vacuum drainage.

Referring now particularly to FIG. 7, and according to another embodiment of the invention, a dressing system 700 for therapeutic wound irrigation and vacuum drainage is illustrated. The system 700 includes a sterile porous substrate 131, which can be fabricated from polyurethane foam, polyvinyl alcohol foam, gauze, felt or other suitable material; a semi-permeable adhesive cover 132 such as that sold under the trademark Avery Denison®; a single lumen drainage tube 122 for the application of vacuum and removal of fluids from the woundsite; and a pliable fluid vessel 601 situated outside and superior to said semi-permeable cover 132. Fluid vessel 601 comprises a self-sealing needle port 603 situated on the superior aspect of the vessel and a regulated drip port 602 situated on the inferior aspect of the vessel. In addition, an annular adhesive ring is provided on the inferior aspect of vessel 601 surrounding regulated drip port 602 for subsequent attachment to drape 132. Needle port 603 permits the introduction of a hypodermic needle 604 for the administration of aqueous topical wound treatment fluids. These aqueous topical fluids can include antibiotics such as Bacitracin or Sulfamide-Acetate; physiologic bleach such as Chlorpactin or Dakins solution; and antiseptics such as Lavasept or Octenisept. Regulated drip port 602 permits fluid within vessel 601 to egress slowly and continuously into porous substrate 131 through a hole in drape 132 whereupon the therapeutic benefits can be imparted to the woundsite. Single-lumen drainage tube 122 provides enough vacuum to keep the dressing 600 at sub-atmospheric pressure and to remove fluids which include the irrigation fluid and wound exudate.

In normal clinical use, dressing 700 is applied to the wound site by first cutting porous substrate 131 to fit the margins of the wound. Next, semi-permeable drape 132 is applied over the woundsite covering the substrate 131 well into the peri-wound area. A hole approximately ¼" diameter is made in drape 132 central to porous substrate 131. Lastly, fluid vessel 601 is attached by adhesive annular ring 605 with drip port 602 aligned with the hole previously cut in drape 132. Once the fluid vessel 601 is properly sealed to the drape 132, a properly prepared hypodermic needle 604 is inserted in self-sealing needle port 603 and fluid vessel 601 subsequently filled with the desired aqueous topical wound treatment solution.

Figure 8:
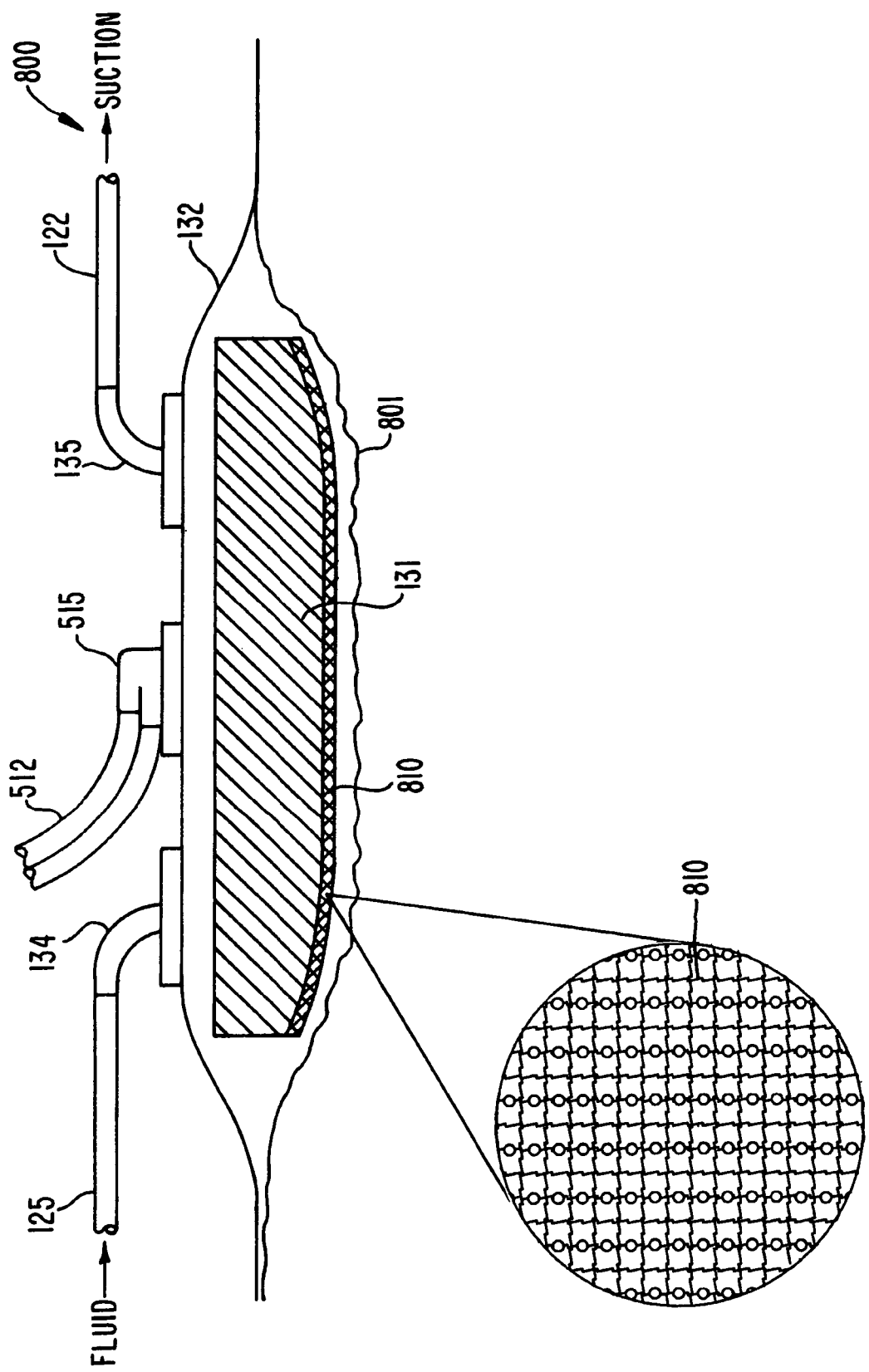
FIG. 8 is an illustration of an application-specific dressing according to an embodiment of the invention incorporating an antibiotic silver mesh between the dressing substrate and wound.

Referring now particularly to FIG. 8, an embodiment of an application-specific dressing 800 of the invention is illustrated. The dressing 800 includes a sterile porous substrate 131, which can be fabricated from polyurethane foam, polyvinyl alcohol foam, gauze, felt or other suitable material; a semi-permeable adhesive cover 132 such as that sold under the trademark Avery Denison®; a single lumen drainage tube 122 for the application of vacuum and removal of fluids from the woundsite; single lumen irrigation tube 125 to facilitate the application of aqueous topical wound fluids to a wound bed 801; and a perforated woven cloth impregnated with metallic silver 810 and bonded to porous substrate 131, for providing an antibiotic action within the wound. Alternatively, and as depicted in FIG. 8, an integrated dressing connector 515 can be used with multi-lumen tubing 512 permitting the wound irrigation and vacuum drainage system to fluidically communicate with dressing 800.

Antibiotic silver layer 810 is fenestrated to permit the unimpeded removal of fluids from the wound bed 801 through the substrate 131 and subsequently through vacuum drainage tubing 122 or 512. In addition, fenestrations in layer 810 permit the even distribution of sub-atmospheric pressure across the wound bed 801 and permit granular tissue formation. Use of silver in a wound as part of a wound dressing is available to the clinician under the trademark(s) Acticoat™ and Silvadene™ and others. Silver can be utilized specifically for burns, stemotomy, radiated fistulas, traumas, and open fractures. Silver is utilized in treating multiple resistant staph aureus (MRSA), preventing odor, reducing incidence of infection and to promote general healing. This embodiment combines the use of silver with wound irrigation and vacuum drainage to provide therapy to the specific wound types identified hereinabove. Antibiotic silver layer 810 can be made of a silver coated woven nylon such as that commercially available under the trademark SilverIon® from Argentum Medical. The material can be fabricated from woven nylon coated with 99.9% pure metallic silver utilizing a proprietary auto-catalytic electroless chemical (reduction-oxidation) plating technology. Alternatively, a non-woven material such as Acti-Coat® Foam from Smith and Nephew, uses two rayon/polyester non-woven inner cores laminated between three layers of High Density Polyethylene (HDPE) Mesh. This material, like the SilverIon® material, can also be fenestrated and used with dressing 800. The antibiotic layer 810 is bonded to porous substrate 131 using a number of available techniques including: in-mold binding, adhesives (such as methyl methacrylate—based bonding agents), and RF or Ultrasonic welding.

Dressing 800 is applied to the wound as described in detail hereinabove. Because of the potential chemical interactions between the various materials used in the construction of dressing 800, attention can be paid to the types of aqueous topical wound fluids used to ensure compatibility.

Figure 9:
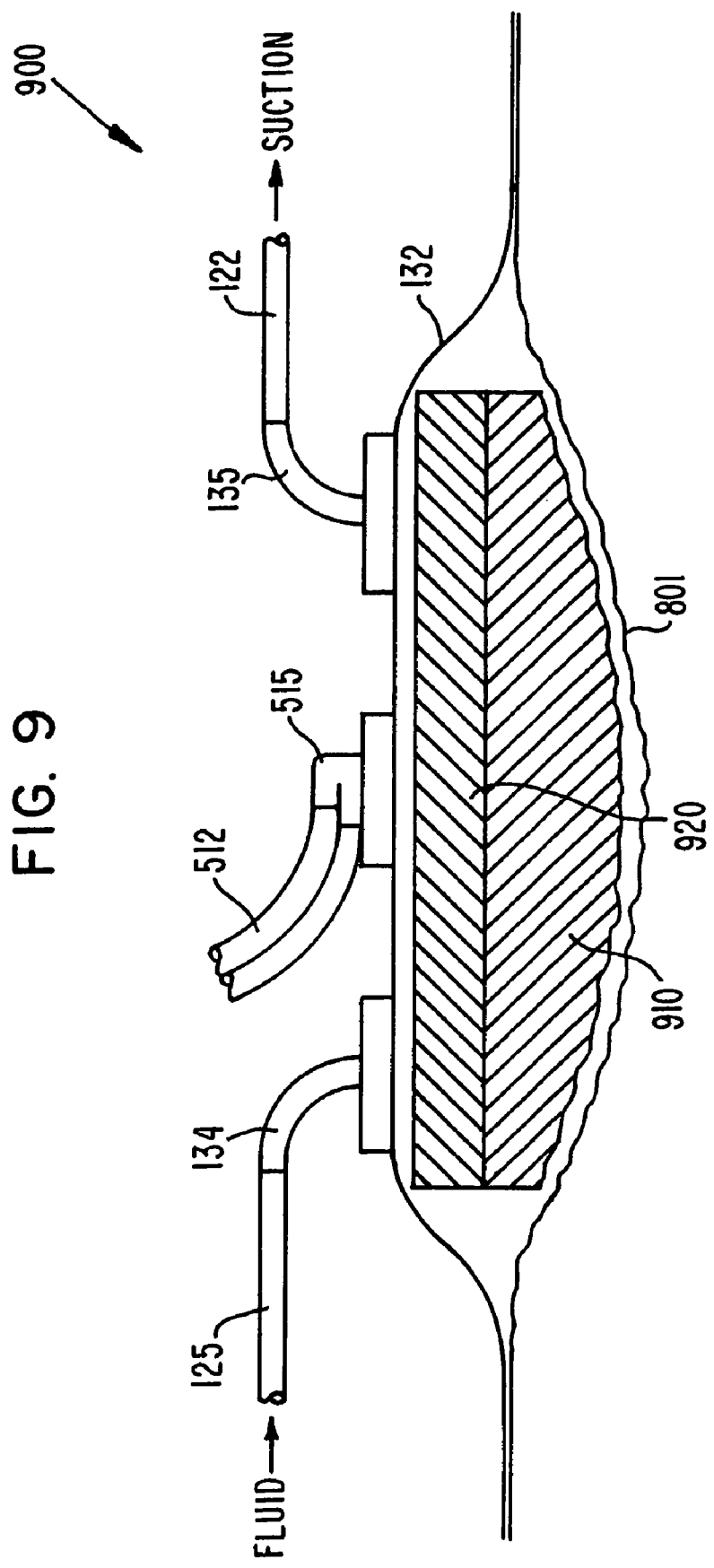
FIG. 9 is an illustration of an application-specific dressing according to an embodiment of the invention incorporating biodegradable materials in the dressing.

Referring now particularly to FIG. 9, another embodiment of an application-specific dressing 900 is illustrated. The dressing 900 includes a sterile porous substrate 910, which can be fabricated from polyurethane foam, polyvinyl alcohol foam, gauze, felt or other suitable material; a semi-permeable adhesive cover 132 such as that sold under the trademark Avery Denison®; a single-lumen drainage tube 122 for the application of vacuum and removal of fluids from the woundsite; single-lumen irrigation tube 125 to facilitate the application of aqueous topical wound fluids to a wound bed 801; and a sterile porous layer of biodegradable material 910 bonded to porous substrate 920, for providing an inducement to healing within the wound. Biodegradable layer 910 is placed substantially within the wound site and is in intimate contact with wound bed 801. Biodegradable layer 910 can be made from myriad materials such as polylactide-co-glycolic acid (PLGA). Alternatively, and as depicted in FIG. 9, an integrated dressing connector 515 can be used with multi-lumen tubing 512 permitting the wound irrigation and vacuum drainage system to fluidically communicate with dressing 900.

Biodegradable layer 910 is porous with similar mechanical characteristics to substrate 920 to permit the unimpeded removal of fluids from the wound bed 801 through the substrate 920 and subsequently through vacuum drainage tubing 122 or 512. In addition, porosity in layer 910 permits the even distribution of sub-atmospheric pressure across the wound bed 801 and encourages granular tissue formation into layer 910. Biodegradable layer 910 is bonded to substrate 920 in such a way that it will readily release from substrate 920 when the dressing is removed from the wound so that the biodegradable layer 910 remains in place and provides a matrix through which tissue growth can occur. The adhesives for removably bonding layers 910 and 920 include, for example, cured silicones, hydrogels and/or acrylics. The thickness of layer 910 can be selected such that ingrowth, which can be as much as 1 mm per day for a typical wound, will not entirely infiltrate layer 910 and invade the removable substrate 920. Alternatively, biodegradable layer 910 can be made up of a matrix of beads adhered together with the same kinds of releasable bonding agents discussed in detail above.

Dressing 900 is suited for wound types that have large defects or voids, which require rapid filling of tissue to provide a foundation for re-epithelialization in the final stages of healing. These application-specific wounds include necrotizing fasciitis, trauma, and iatrogenic wounds such as would occur with certain oncological procedures. In addition to addressing soft tissue repairs, dressing 900 can be configured to heal large bone defects such as those that result from surgical treatment of osteocarcinoma, and trauma where significant bone loss occurs. For these types of wounds, biodegradable layer 910 would be made of a rigid material that would serve as a matrix to encourage osteoblast invasion and bone growth into the defect. As described above, the material that makes up layer 910 would remain in the wound after the dressing is removed.

Dressing 900 can be applied as described above in the previous embodiments; the only significant difference being that during dressing changes, the biodegradable portion, layer 910, would remain in the wound. With a conventional dressing change, typically all the dressing material and debris would be removed to prevent possibility of foreign body reaction and infection. Here, subsequent dressing would be applied over the previous dressing's biodegradable layer 910 facilitating tissue grown therein. Once a suitable foundation of granular tissue has formed in the wound, the clinician would discontinue use of the biodegradable dressing substituting instead one of the other dressing materials and configurations disclosed hereinabove until the wound was completely healed.

Referring now particularly to FIG. 10, an embodiment of an application-specific dressing 1000 is illustrated. The dressing 1000 includes a sterile porous substrate 1030, which can be fabricated from polyurethane foam, polyvinyl alcohol foam, gauze, felt or other suitable material; a semi-permeable adhesive cover 132 such as that sold under the trademark Avery Denison®; a single-lumen drainage tube 122 for the application of vacuum and removal of fluids from the wound-site; single-lumen irrigation tube 125 to facilitate the application of aqueous topical wound fluids to a wound bed 801; a sterile porous layer of biocompatible material 1020 releasably bonded to porous substrate 1030; and an autologous graft layer 1010 integrated with biocompatible material 1020 for stimulating a healing response in a wound. Biocompatible layer 1020 and autologous graft layer 1010 are placed substantially within the wound site with autologous graft layer 1010 in intimate contact with wound bed 801. Alternatively, and as depicted in FIG. 10, an integrated dressing connector 515 can be used with multi-lumen tubing 512 permitting the wound irrigation and vacuum drainage system to fluidically communicate with dressing 1000.

Biocompatible layer 1020 can be an acellular dermal matrix manufactured from donated human skin tissue, which is available under the trademark AlloDerm® from LifeCell Inc. This dermal matrix has been processed to remove all the cells that lead to tissue rejection while retaining the original biological framework. Cells taken from the patient or other molecules can subsequently be seeded into this matrix forming layer 1010. These cells or molecules can include but are not limited to: fibroblasts, platelet derived growth factor (PDGF), Transforming Growth Factor Alpha (TGF-α), Transforming Growth Factor Beta (TGF-β) and other cytokines. PDGF is a polypeptide hormone derived from platelets, which stimulate fibroblasts to migrate and lay down collagen and fibronectin thereby initiating wound repair. If targeted cells are taken from the patient and seeded into biocompatible layer 1020 forming layer 1010, the body will not reject them. In addition to seeding the inferior aspect of layer 1020 with the above described autologous cells or molecules, the superior aspect of layer 1020 can be seeded with live dermal cells taken from the patient using a mesh graft or micrografting technique. The configuration of two graft layers 1010 enclosing a biocompatible layer 1020 permits intrinsic tissue regeneration in such a way as to minimize the formation of scar tissue and maintain original structure.

Dressing 1000 is designed for wound types that require reconstruction where the newly regenerated tissue has cellular structure similar to the original tissue. These application-specific wounds include surgical dehiscence, burns, and diabetic ulcers.

In normal clinical use, the dressing 1000 would be prepared on a patient-by-patient basis first by harvesting the requisite cells from donor sites followed by processing (when necessary to derive bioactive components) then seeding the cells or cytokines into the biocompatible layer 1020. Special care and handling can be used in the preparation of dressing 1000 to promote preservation of the bioactive components and maintenance of the sterility of the dressing. Once the dressing has been properly configured for the patient, it is applied as described in detail hereinabove. When dressing changes occur, biocompatible layer 1020 and autologous graft layer 1010 will remain in the wound much like the biodegradable dressing 900 also described in detail above.

The above described embodiments are set forth by way of example and are not limiting. It will be readily apparent that obvious modifications, derivations and variations can be made to the embodiments. For example, the vacuum pump(s) 105 and 107 described hereinabove as either a diaphragm or piston-type could also be one of a syringe based system, bellows, or even an oscillating linear pump. Similarly, the vacuum control algorithm 150 described in detail above as multi-modal could be one of many other algorithms well known to anyone of ordinary skill in the art. Likewise, use of PLGA as a biodegradable substance for a component of dressing 900 could be one of many different types of biodegradable materials commonly used for implantable medical devices. Accordingly, the claims appended hereto should be read in their full scope including any such modifications, derivations and variations.

The invention claimed is:

1. An apparatus, comprising:
a fluid permeable dressing;
a cover membrane configured to extend over the fluid permeable dressing;
a tube coupled to the fluid permeable dressing, the tube configured to apply suction through the fluid permeable dressing; and
a fluid vessel integrated with the cover membrane and disposed between the fluid permeable dressing and the cover membrane, the fluid vessel including an inlet port and an outlet port fluidically coupled to the fluid permeable dressing, the outlet port configured to deliver a treatment fluid to the fluid permeable dressing.

2. The apparatus of claim 1, wherein the inlet port of the fluid vessel is a self-sealing needle port.

3. The apparatus of claim 1, wherein the outlet port of the fluid vessel is a regulated drip port.

4. The apparatus of claim 1, wherein the inlet port is spaced less than six inches from the outlet port.

5. The apparatus of claim 1, further comprising a collection canister configured to receive exudate from the fluid permeable dressing via the tube.

6. The apparatus of claim 1, wherein the fluid vessel is coupled to the cover membrane using at least one of a heat weld, a radio frequency (RF) weld, or an adhesive.

7. The apparatus of claim 1, wherein the cover membrane has an outer boundary that surrounds the outer boundary of the fluid vessel.

8. The apparatus of claim 1, wherein the fluid vessel includes a fluid vessel wall having an outer surface substantially enclosed by the cover membrane when the cover membrane extends over the fluid permeable dressing.

9. The apparatus of claim 1, further comprising:
a vacuum pump coupled to the tube, the vacuum pump configured to apply suction to the fluid permeable dressing through the tube, the vacuum pump having a first configuration in which suction is applied to the fluid permeable dressing at a first rate, the vacuum pump having a second configuration in which suction is applied to the fluid permeable dressing at a second rate less than the first rate.

10. The apparatus of claim 1, wherein the entire fluid permeable dressing is pliable.

11. An apparatus, comprising:
a fluid permeable dressing having a region configured to be coupled to a suction source;
a cover membrane configured to extend over the fluid permeable dressing, the cover membrane having an outer boundary; and
a fluid vessel configured to contain a treatment fluid, the fluid vessel including an inlet port configured to receive a fluid and an outlet port fluidically coupled to the fluid permeable dressing, the fluid vessel having an outer boundary surrounded by the outer boundary of the cover membrane, the fluid vessel having a width in a dimension substantially parallel with a plane defined by an upper surface of the fluid permeable dressing and a depth in a dimension substantially perpendicular to the plane defined by the upper surface, the width being greater than the depth.

12. The apparatus of claim 11, further comprising:
a tube coupled to the region of the fluid permeable dressing, the tube configured to apply suction through the fluid permeable dressing.

13. The apparatus of claim 11, wherein the fluid vessel is coupled directly to at least one of an outer surface of the cover membrane or an inner surface of the cover membrane.

14. The apparatus of claim 11, wherein the inlet port of the fluid vessel is a self-sealing needle port.

15. The apparatus of claim 11, wherein the outlet port of the fluid vessel is a regulated drip port.

16. The apparatus of claim 11, wherein the fluid vessel is disposed between the fluid permeable dressing and the cover membrane.

17. The apparatus of claim 11, wherein the inlet port is spaced less than six inches from the outlet port.

18. The apparatus of claim 11, further comprising a collection canister configured to receive and store exudate from the fluid permeable dressing.

19. The apparatus of claim 11, wherein the fluid vessel includes a fluid vessel wall having an outer surface substantially enclosed by the cover membrane when the cover membrane extends over the fluid permeable dressing.

20. An apparatus, comprising:
a fluid permeable dressing having a region configured to be coupled to a suction source;
a cover membrane configured to extend over the fluid permeable dressing; and
a fluid vessel configured to contain a treatment fluid, the fluid vessel coupled to the cover membrane, the fluid vessel including an outlet port fluidically coupled to the fluid permeable dressing, the outlet port configured to control a delivery of the treatment fluid to the fluid permeable dressing, the fluid vessel including an outer boundary substantially coterminous with an outer boundary of the fluid permeable dressing.

21. The apparatus of claim 20, wherein the fluid vessel is coupled directly to the cover membrane using at least one of a heat weld, a radio frequency (RF) weld, or an adhesive.

22. The apparatus of claim 20, wherein the fluid vessel is coupled directly to at least one of an outer surface of the cover membrane or an inner surface of the cover membrane.

23. The apparatus of claim 20, wherein the fluid vessel includes an inlet port, the inlet port of the fluid vessel is a self-sealing needle port.

24. The apparatus of claim 20, wherein the outlet port of the fluid vessel is a regulated drip port.

25. The apparatus of claim 20, wherein the fluid vessel is disposed between the fluid permeable dressing and the cover membrane.

26. The apparatus of claim 20, wherein the fluid vessel includes an inlet port, the inlet port is spaced less than six inches from the outlet port.

27. The apparatus of claim 20, further comprising a collection canister configured to receive and store exudate from the fluid permeable dressing.

28. The apparatus of claim 20, wherein the outlet port of the fluid vessel is directly adjacent to at least one of the cover membrane or the fluid permeable dressing.

* * * * *